United States Patent
Geroni et al.

(12)

(10) Patent No.: US 6,403,563 B1
(45) Date of Patent: Jun. 11, 2002

(54) ANTITUMOR COMPOSITION CONTAINING A SYNERGISTIC COMBINATION OF AN ANTHRACYCLINE DERIVATIVE WITH A CAMPTOTHECIN DERIVATE

(75) Inventors: Cristina Geroni; Marina Ripamonti; Michele Caruso; Antonino Suarato, all of Milan (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/646,096

(22) PCT Filed: Mar. 19, 1999

(86) PCT No.: PCT/EP99/01897

§ 371 (c)(1),
(2), (4) Date: Sep. 20, 2000

(87) PCT Pub. No.: WO99/48503

PCT Pub. Date: Sep. 30, 1999

(30) Foreign Application Priority Data

Mar. 24, 1998 (GB) ............................................. 9806324

(51) Int. Cl.⁷ ............................................... A61K 31/70

(52) U.S. Cl. ......................................................... 514/34
(58) Field of Search ............................................ 514/34

(56) References Cited

U.S. PATENT DOCUMENTS 5,496,808 A * 3/1996 Bargiotti et al. ............... 514/34
5,532,218 A * 7/1996 Bargiotti et al. ............... 514/34

OTHER PUBLICATIONS

Zhang et al, Asia Pac. J. Pharmacol. 1992, 191–5.*
Eder et al, Cancer Clemother. Pharmacol., 1998 42(s).*

* cited by examiner

*Primary Examiner*—Elli Peselev
(74) *Attorney, Agent, or Firm*—Oblon, Spivak, McClelland, Maier & Neustadt, P.C.

(57) ABSTRACT

The combination of 4-demethoxy-3'-deamino-3'-aziridinyl-4'-methansulfonyl daunorubicin or 4-demethoxy-N,N-bis(2-chloroethyl)-4'-methansulfonyl daunorubicin together with an antineoplastic topoisomerase I inhibitor yields preparations exhibiting anti-cancer effects. These preparations can be used in the treatment of tumors and especially 4-demethoxy-3'-deamino-3'-aziridinyl-4'-methansulfonyl daunorubicin in the treatment of brain tumors.

10 Claims, No Drawings

ANTITUMOR COMPOSITION CONTAINING A SYNERGISTIC COMBINATION OF AN ANTHRACYCLINE DERIVATIVE WITH A CAMPTOTHECIN DERIVATE

This application claims priority to PCT Application EP 99/01897 filed Mar. 19, 1999 and Application No. GB 9806324.1 filed Mar. 24, 1998.

The present invention relates in general to the field of cancer treatment and, more particularly, provides an antitumor composition comprising an alkylating anthracycline and a topoisomerase I inhibitor, having a synergetic antineoplastic effect.

The present invention provides, in a first aspect, a pharmaceutical composition for use in antineoplastic therapy in mammals, including humans, comprising
an anthracycline of formula Ia or Ib:

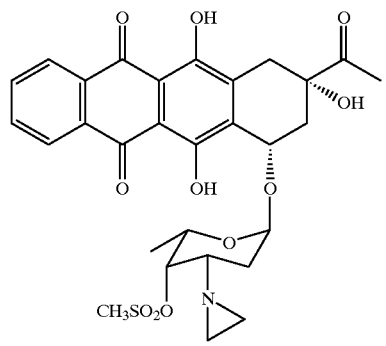

Ia

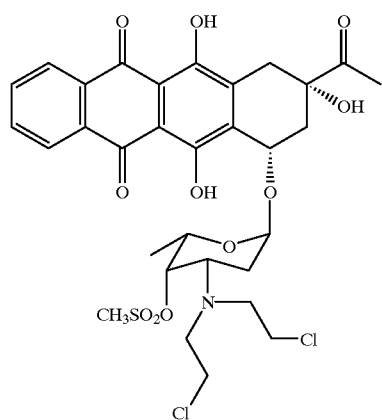

Ib an antineoplastic topoisomerase I inhibitor, and a pharmaceutically acceptable carrier or excipient.

The chemical names of the anthracyclines of formula Ia and Ib are 4-demethoxy-3'-deamino-3'-aziridinyl-4'-methansulfonyl daunorubicin (Ia) and 4-demethoxy-N,N-bis (2-chloroethyl)-4'-methansulfonyl daunorubicin (Ib). These anthracyclines were described in Anticancer Drug Design (1995), vol. 10, 641-653, and claimed respectively in U.S. Pat. No. 5,532,218 and U.S. Pat. No. 5,496,800. Both compounds intercalate into DNA via the chromophore and alkylate guanine at $N^7$ position in DNA minor groove via their reactive moiety on position 3' of the amino sugar. Compounds Ia and Ib are able to circumvent the resistance to all major classes of cytotoxics, indicating that the compounds represent a new class of alkylating drugs. Topoisomerase I inhibitor are described in various scientific publications, see for example the review of M. L. Rothenberg, "Topoisomerase I inhibitors: Review and update", Annals of Oncology, 8: 837–855, 1997.

Typically, a topoisomerase I inhibitor is camptothecin or its derivative substituted on the quinoline ring or at position 20-OH. Examples of specific topoisomerase I inhibitor to be used in the present invention are: camptothecin, 9-aminocamptothecin, irinotecan (CPT-11), topotecan, 7-ethyl-10-hydroxy-camptothecin, GI 147211 and 9-nitrocamptothecin. All these camptothecin derivatives are known, see for example Medicinal Research Reviews, Vol 17, No. 4, 367–425, 1997.

Irinotecan (CPT-11) is the preferred topoisomerase I inhibitor to be used in the present invention. The present invention also provides a product comprising an anthracycline of formula Ia or Ib as defined above and an antineoplastic topoisomerase I inhibitor, as combined preparation for simultaneous, separate or sequential use in antitumor therapy.

A further aspect of the present invention is to provide a method of treating a mammal including humans, suffering from a neoplastic disease state comprising administering to said mammal an anthracycline of formula Ia or Ib as defined above and an antineoplastic topoisomerase I inhibitor, in amounts effective to produce a synergetic antineoplastic effect.

The present invention also provides a method for lowering the side effects caused by antineoplastic therapy with an antineoplastic agent in mammals, including humans, in need thereof, the method comprising administering to said mammal a combination preparation comprising an antineoplastic topoisomerase I inhibitor as defined above and an anthracycline of formula Ia or Ib, as defined above, in amounts effective to produce a synergetic antineoplastic effect.

By the term "a synergetic antineoplastic effect" as used hererin is meant the inhibition of the growth tumor, preferably the complete regression of the tumor, administering an effective amount of the combination of an anthracycline of formula Ia or Ib as defined above and a topoisomerase I inhibitor to mammals, including human.

By the term "administered" or "administering" as used herein is meant parenteral and/or oral administration. By "parenteral" is meant intravenous, subcutaneus and intramuscolar administration. In the method of the subject invention, the anthracycline may be administered simultaneously with the compound with the topoisomerase I inhibitor activity, for example of the camptothecin analog class, or the compounds may be administered sequentially, in either order. It will be appreciated that the actual preferred method and order of administration will vary according to, inter alia, the particular formulation of the anthracycline of formula Ia or Ib being utilized, the particular formulation of the topoisomerase I inhibitor, such as one of the camptothecin analog class, being utilized, the particular tumor model being treated, and the particular host being treated.

In the method of the subject invention, for the administration of the anthracycline of formula Ia or Ib, the course of therapy generally employed is from about 0.1 to about 200 $Mg/m^2$ of body surface area. More preferably, the course therapy employed is from about 1 to about 50 $mg/M^2$ of body surface area.

In the method of the subject invention, for the administration of the topoisomerase I inhibitor the course of therapy generally employed is from about 1 to about 1000 $mg/M^2$ of body surface area for about one to about five consecutive days. More preferably, the course therapy employed is from about 100 to about 500 $mg/m^2$ of body surface area per day for about five consecutive days.

The antineoplastic therapy of the present invention is in particular suitable for treating breast, ovary lung, colon, kidney and brain tumors in mammals, including humans. In a further aspect, the present invention is directed to the preparation of a pharmaceutical composition containing an effective amount of an anthracycline of formula Ia for the treatment of brain tumors, as well as to the use of an anthracycline of formula Ia for the treatment of brain tumors. As a matter of fact, the anthracycline of formula Ia crosses the blood brain barrier and showed activity against intracranially implanted tumors.

As stated above, the effect of an anthracycline of formula Ia or Ib and a topoisomerase I inhibitor, such as camptothecin derivative, is significantly increased without a parallel increased toxicity. In other words, the combined therapy of the present invention enhances the antitumoral effects of the alkylating anthracycline and of the topoisomerase I inhibitor and thus yields the most effective and least toxic treatment for tumors. The superadditive actions of the combination preparation of the present invention are shown for instance by the following in vivo tests, which are intended to illustrate but not to limit the present invention.

Table 1 shows the antileukemic activity on disseminated L1210 murine leukemia obtained combining Ia with CPT-11. At the dose of 20 mg/kg of CPT-11 alone (days +1,2) and at the doses of 2.9 and 3.8 mg/kg of Ia alone (day +3) were associated, without toxicity, with ILS% values of 100, 92 and 108, respectively; combining CPT-11 and Ia at the same doses of 2.9 with the same schedule an increase of activity with ILS% values of 375 (with 3/10 cured mice) and >950 (with 8/10 cured mice) was observed, indicating a synergistic effect. For these experiments Ia was solubilized in [Cremophor®/EtOH=6.5:3.5]/[normal saline]=20/80 v/v, while CPT-11 was solubilized in water.

Activity Against Brain Implanted Tumor Model

Brain tumors/metastases are generally unresponsive largely because cytotoxic drugs fail to cross the blood brain barrier. Since data showed that the anthracycline of formula Ia crosses the blood brain barrier, the antitumor efficacy of the anthracycline of formula Ia was tested against intracranially implanted P388 tumor cells in mice. The compound was administered i.v. on days 1,5,9. Results reported in Tab. 2 show that the anthracycline of formula Ia presented good antitumor activity as expressed by ILS% value of 46 at the optimal cumulative dose of 8.1 mg/kg.

TABLE 1

Antileukemic activity against disseminated L1210[1] of Ia in combination with CPT-11

| Compound | Treatment schedule | Dose[2] (mg/kg/day) | ILS %[3] | Tox[4] | LTS[5] |
|---|---|---|---|---|---|
| CPT-11 | iv + 1, 2 | 20 | 100 | 0/10 | 1/10 |
| Ia | iv + 3 | 2.9 | 92 | 0/10 | 0/10 |
|  |  | 3.8 | 108 | 0/10 | 0/10 |
| CPT-11 + Ia | iv + 1, 2 | 20 | 375 | 0/10 | 3/10 |
|  | iv + 3 | 2.9 |  |  |  |
| CPT-11 + Ia | iv + 1, 2 | 20 | >950 | 0/10 | 8/10 |
|  | iv + 3 | 3.8 |  |  |  |

[1]L1210 leukemia cells ($10^5$/mouse) are injected iv on day 0.
[2]Treatment is given iv starting on day 1 after tumor transplantation (day 0).
[3]Increase in life span: [(median survival time of treated mice/median survival time of controls) × 100] − 100.
[4]Number of toxic deaths/number of mice.
[5]Long Term Survivors (>60 days) at the end of the experiments.

TABLE 2

Activity against intracranially transplanted P388 murine leukemia[1]

| Compound | Dose[2] (mg/kg/day) | ILS %[3] | Tox[4] |
|---|---|---|---|
| Ia | 2.1 | 44 | 0/20 |
|  | 2.7 | 46 | 1/20 |

[1]P388 leukemia cells ($10^4$/mouse) injected intracranially on day 0.
[2]Treatment is given i.v. on day 1, 5, 9 after tumor transplantation (day 0). Ia solubilized in Tween 80 at 10%
[3]Increase in life span: [(median survival time of treated mice/median survival time of controls) × 100] − 100.
[4]Number of toxic deaths/number of mice.

The entire contents of the priority documents are hereby incorporated by reference.

What is claimed is:

1. A composition comprising an anthracycline of formula Ia or Ib:

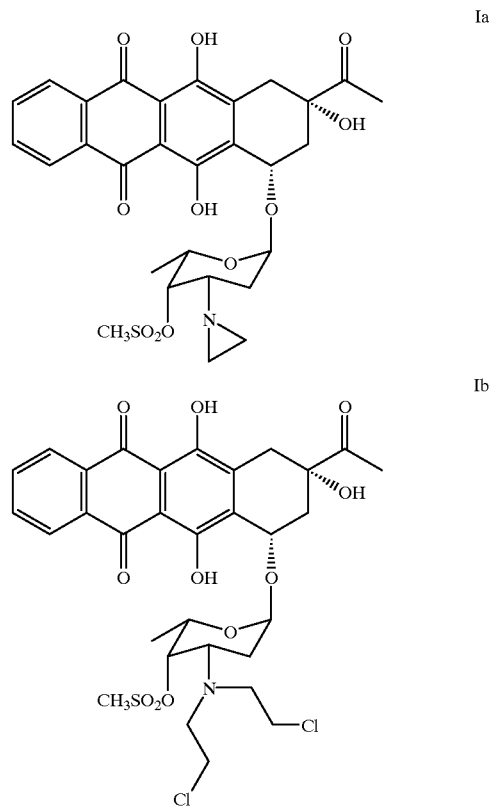

and an antineoplastic topoisomerase I inhibitor, wherein said anthracycline and said topoisomerase are present in a synergistically anti-neoplastic effective amount.

2. A composition according to claim 1 wherein the topoisomerase I inhibitor is camptothecin, 9-aminocamptothecin, irinotecan (CPT-11), topotecan, 7-ethyl-10-hydroxy-camptothecin, GI 147211 or 9-nitrocamptothecin.

3. A pharmaceutical composition comprising a pharmaceutically acceptable carrier or excipient and, as active ingredient, an anthracycline of formula Ia or Ib as defined in claim 1 and an antineoplastic topoisomerase I inhibitor.

4. A composition according to claim 3 wherein the topoisomerase I inhibitor is camptothecin, 9-aminocamptothecin, irinotecan (CPT-11), topotecan, 7-ethyl-10-hydroxy-camptothecin, GI 147211 or 9-nitrocamptothecin.

5. A method for treating a mammal suffering from a neoplastic disease state, said method comprising administering the composition claimed in claim 1 to said mammal a synergistically anti-neoplastic effective amount.

6. A pharmaceutical composition comprising the composition claimed in claim 1 and a pharmaceutically acceptable carrier or excipient.

7. The method for treating a mammal suffering from a neoplastic disease state as claimed in claim 5, wherein the topoisomerase I inhibitor is camptothecin, 9-aminocamptothecin, irinotecan (CPT-11), topotecan, 7-ethyl-10-hydroxy-camptothecin, GI 147211 or 9-nitrocamptothecin.

8. A pharmaceutical composition for treating brain tumors comprising, a synergistically anti-neoplastic effective amount of the anthracycline of formula Ia as claimed in claim 1 and an antineoplastic topoisomerase I inhibitor, and a pharmaceutically acceptable carrier or excipient.

9. The method as claimed in claim 5, wherein the mammal is a human.

10. The method as claimed in claim 9, wherein the mammal is a human.

* * * * *